United States Patent
Burdon et al.

(10) Patent No.: US 6,592,696 B1
(45) Date of Patent: Jul. 15, 2003

(54) METHOD FOR FABRICATING A MULTILAYERED STRUCTURE AND THE STRUCTURES FORMED BY THE METHOD

(75) Inventors: Jeremy W. Burdon, Albuquerque, NM (US); Rong-Fong Huang, Albuquerque, NM (US); David Wilcox, Albuquerque, NM (US); Nicholas J. Naclerio, Barrington, IL (US)

(73) Assignee: Motorola, Inc., Schaumburg, IL (US)

( * ) Notice: Subject to any disclaimer, the term of this patent is extended or adjusted under 35 U.S.C. 154(b) by 0 days.

(21) Appl. No.: 09/235,081

(22) Filed: Jan. 21, 1999

Related U.S. Application Data (60) Provisional application No. 60/103,701, filed on Oct. 9, 1998.

(51) Int. Cl.[7] .......................... B32B 31/12; B32B 31/26; H05K 3/46
(52) U.S. Cl. ............................... 156/89.12; 156/89.11; 156/89.16; 156/89.23; 156/219; 156/272.8; 156/312
(58) Field of Search ............................ 156/89.11, 89.12, 156/89.16, 89.23, 219, 272.8, 252, 312; 427/96; 29/851

(56) References Cited

U.S. PATENT DOCUMENTS

| | | | |
|---|---|---|---|
| 3,293,072 A | | 12/1966 | Doolittle et al. |
| 3,506,473 A | | 4/1970 | Ettre et al. |
| 3,574,029 A | | 4/1971 | Ettre et al. |
| 3,598,679 A | | 8/1971 | Ettre et al. |
| 3,948,706 A | * | 4/1976 | Schmeckenbecher |
| 3,956,052 A | * | 5/1976 | Koste et al. |
| 3,991,029 A | | 11/1976 | Adelman |
| 4,118,237 A | | 10/1978 | Beall et al. |
| 4,523,121 A | | 6/1985 | Takahashi et al. |
| 4,551,357 A | * | 11/1985 | Takeuchi ..................... 427/96 |

(List continued on next page.)

FOREIGN PATENT DOCUMENTS

| | | | |
|---|---|---|---|
| DE | 197 25 948 A1 | | 12/1998 |
| EP | 0 649 008 A2 | | 10/1994 |
| EP | 0 744 389 A1 | | 11/1996 |
| EP | 0 870 541 A2 | | 10/1998 |
| JP | 53-49264 | * | 5/1978 |
| JP | 63-42147 | * | 2/1988 |
| JP | 63-239999 | * | 10/1988 |
| JP | 2-117117 | * | 5/1990 |
| JP | 2-166793 | * | 6/1990 |
| JP | 2-219603 | * | 9/1990 |
| JP | 3-148196 | * | 6/1991 |
| JP | 4-18795 | * | 1/1992 |
| JP | 4-114961 | * | 4/1992 |
| JP | 5-267844 | * | 10/1993 |
| JP | 6-104572 | * | 4/1994 |
| JP | 6-152135 | * | 5/1994 |
| JP | 6-290987 | * | 10/1994 |
| JP | 8-108422 | * | 4/1996 |
| JP | 8-267421 | * | 10/1996 |

OTHER PUBLICATIONS

Morton L. Topfer "Chapter 3:Technology" Thick–Film Microelectronics, pp. 40–59 (1977).
Microsphere Selection Guide, Bangs Laboratories, Inc. Product Information Bulletin. Mar., (1999).
Bangs, L. B., The Latex Course (Apr. 1996), Immunological Applications of Microspheres.

(List continued on next page.)

Primary Examiner—Curtis Mayes
(74) Attorney, Agent, or Firm—Douglas W. Gilmore (57) ABSTRACT

A method for fabricating a multilayered structure out of sheets of green-tape without the application of high pressures includes the step of applying an adhesive to the sheets of green-tape. Selection of an adhesive with a polymer that decomposes at a higher temperature than the binder present in the green-tape promotes stability of the interfaces during the firing process and promotes void-free sintering within the interfacial regions. A multilayered structure with internal electrical conduction pathways and with internal vias, channels, and cavities may be fabricated by this method

28 Claims, 5 Drawing Sheets

U.S. PATENT DOCUMENTS

| | | | |
|---|---|---|---|
| 4,610,741 A | | 9/1986 | Mase et al. |
| 4,737,208 A | | 4/1988 | Bloechle et al. |
| 4,806,295 A | | 2/1989 | Trickett et al. |
| 4,833,000 A | | 5/1989 | Trickett et al. |
| 4,929,295 A | | 5/1990 | Kohno et al. |
| 4,939,021 A | * | 7/1990 | Aoki et al. |
| 4,985,098 A | | 1/1991 | Kohno et al. |
| 4,991,283 A | | 2/1991 | Johnson et al. |
| 5,008,151 A | | 4/1991 | Tominaga et al. |
| 5,089,071 A | | 2/1992 | Tominaga et al. |
| 5,174,842 A | | 12/1992 | Hamuro et al. |
| 5,176,771 A | | 1/1993 | Bravo et al. |
| 5,254,191 A | | 10/1993 | Mikeska et al. |
| 5,261,986 A | * | 11/1993 | Kawabata et al. |
| 5,265,327 A | | 11/1993 | Faris et al. |
| 5,271,150 A | | 12/1993 | Inasaka |
| 5,312,674 A | | 5/1994 | Haertling et al. |
| 5,358,593 A | | 10/1994 | Hamuro et al. |
| 5,435,875 A | | 7/1995 | Saitoh et al. |
| 5,478,420 A | | 12/1995 | Gauci et al. |
| 5,480,614 A | | 1/1996 | Kamahori |
| 5,534,092 A | * | 7/1996 | Ogawa et al. |
| 5,534,328 A | | 7/1996 | Ashmead et al. |
| 5,538,582 A | | 7/1996 | Natarajan et al. |
| 5,540,884 A | | 7/1996 | Chiao |
| 5,565,729 A | | 10/1996 | Faris et al. |
| 5,585,069 A | | 12/1996 | Zanzucchi et al. |
| 5,595,712 A | | 1/1997 | Harbster et al. |
| 5,601,673 A | | 2/1997 | Alexander |
| 5,603,351 A | | 2/1997 | Cherukuri et al. |
| 5,607,535 A | | 3/1997 | Tsukada et al. |
| 5,611,214 A | | 3/1997 | Wegeng et al. |
| 5,614,053 A | | 3/1997 | Toudo et al. |
| 5,632,876 A | | 5/1997 | Zanzucchi et al. |
| 5,639,508 A | | 6/1997 | Okawa et al. |
| 5,676,788 A | | 10/1997 | Natarajan et al. |
| 5,681,410 A | | 10/1997 | Takeuchi et al. |
| 5,683,535 A | | 11/1997 | Karr |
| 5,707,476 A | | 1/1998 | Bezama et al. |
| 5,728,244 A | * | 3/1998 | Nanataki et al. |
| 5,746,874 A | | 5/1998 | Natarajan et al. |
| 5,753,060 A | | 5/1998 | Mori |
| 5,759,320 A | | 6/1998 | Natarajan et al. |
| 5,779,833 A | | 7/1998 | Cawley et al. |
| 5,785,800 A | | 7/1998 | Natarajan et al. |
| 5,792,379 A | | 8/1998 | Dai et al. |
| 5,795,545 A | | 8/1998 | Koripella et al. |
| 5,811,062 A | | 9/1998 | Wegeng et al. |
| 5,821,181 A | | 10/1998 | Bethke et al. |
| 5,842,106 A | | 11/1998 | Thaler et al. |
| 5,855,803 A | | 1/1999 | Bailey et al. |
| 5,858,193 A | | 1/1999 | Zanzucchi et al. |
| 5,858,195 A | | 1/1999 | Ramsey |
| 5,860,202 A | | 1/1999 | Okawa et al. |
| 5,863,708 A | | 1/1999 | Zanzucchi et al. |
| 5,939,291 A | | 8/1999 | Loewy et al. |
| 5,961,930 A | | 10/1999 | Chatterjee et al. |
| 5,961,932 A | | 10/1999 | Ghosh et al. |
| 5,965,092 A | | 10/1999 | Chatterjee et al. |
| 5,971,355 A | | 10/1999 | Biegelsen et al. |
| 5,976,472 A | | 11/1999 | Chatterjee et al. |
| 5,985,119 A | | 11/1999 | Zanzucchi et al. |
| 5,993,750 A | | 11/1999 | Ghosh et al. |

OTHER PUBLICATIONS

Belgrader P. et al., "Rapid pathogen detection using a microchip PCT array instrument", *Clinical Chemistry*, vol. 44, No. 10, pp 2191–2194, (1998).

Espinoza–Vallejos, P. et al., "MESO (Intermediate)–Scale electromechanical systems for the measurment and control of sagging in LTCC structures", Med. Res. Soc. Symp. Pros., vol. 518, pp. 73–79 (1998).

Fuhr, G. et al., "Pumping of water solutions in microfabricated electrohydrodynamic systems" Parts of the conference on Micro Electro Mechanical Systems, pp. 25–30 (1992).

Gongora–Rubio, M. et al. "The utilization of low temperature co0fired ceramics (LTCC–ML) technology for meso–scale EMS, a simple thermistor based flow sensor", Sensors and Actuators, vol. 73, pp. 215–221 (1999).

Gongora–Rubio, M. et al., "A Meso–scale Electro–magnetically actuated normally closed valve realized on LTCC tapes", Part of the SPIE Conference on Microfluidic Devices and Systems II, Sep. 1999, SPIE, vol. 3877, pp. 230–239.

Gongora–Rubio, M. et al., "A simple thermistor based flow sensor using the LTCC–ML technology", Quimica Analitica, vol. 18, pp. 30–32 (1999).

Gui, Z. et al., Influence of additives on sintering processing and properties of high performance piezoelectric ceramics, Solic State Phenomina, vol.s 25 & 26, pp. 309–316 (1992).

Kim, M. et al., "The fabrication of flow conduits in ceramic tapes and the measurement of fluid flow through these conduits" DSC–vol. 66, Micro–Electro–Mechanical Systems (MEMS) –pp. 171–177 (1998).

Kricka, Larry J., "Revolution on a square centimeter" Nature Biotechnology, vol. 16, pp. 513–514 (1998).

Liu, J. H. et al., "Study of thick–film pH sensors" Sensors and Actuatoors $B_1$, vol. 13–14, pp. 566–567 (1993).

Manz, Andreas, "Electroosmotic pumping and electrophoretic separations for miniaturized chemical analysis systems" J. Micromech. Microeng., vol. 4, pp. 257–265, (1994).

Mistler, Richard E., "Tape Casting: The Basic Process for Meeting the Needs of the Electronics Industry" Ceramic Bulletin, vol. 69, No. 6, pp. 1022–1026, (1990).

Provamce, J.D. "Performance Review of Thick Film Materials" reprinted from Insulation Circuits (Apr. 1977).

Santiago–Avilés, J. J. et al., "The utilization of low temperature co–fired ceramic tapes for 3 dimensional meso–scale fabrication" Química Analítica, vol. 18, [Suppl 1]: pp. 33–34 (1999)

Sinclair, Bob "To Bead of Not to Bead: Applications of Magnetic Bead Technology" The Scientist, pp. 16–19, Jun. 22, (1998).

Waters, Larry C. et al., "Microchip Device for Cell Lysis, Multiplex PCR Amplification, and Electrophoretic Sizing" Analytical Chemistry, vol. 70, No. 1, pp. 158–162 (1998).

* cited by examiner

METHOD FOR FABRICATING A MULTILAYERED STRUCTURE AND THE STRUCTURES FORMED BY THE METHOD

CROSS-REFERENCE TO RELATED APPLICATIONS

This application claims the benefit of U.S. Provisional Application No. 60/103,701, filed Oct. 9, 1998.

BACKGROUND OF THE INVENTION

1. Field of the Invention

This invention relates to the field of multilayered structure fabrication. More particularly, this invention relates to a multilayered structure and a method for fabricating a multilayered structure from layers of green-tape, wherein an adhesive is applied to the layers of green-tape to bind the layers together.

2. Description of Related Art

Multilayered structures, such as multilayered ceramic structures, find application as electronic devices, such as ceramic capacitors, multilayered ceramic integrated circuits (MCIC), multichip modules, integrated circuit packaging, high temperature sensors (such as exhaust gas sensors), fuel cells, and fuel cell reformer systems. Multilayered structures also find application as microchannel devices, such as secondary electron multipliers and microfluidic devices.

Such multilayered structures are often made by laminating together layers of green-tape, typically ceramic green-tape, and then firing the laminated layers to form the finished structure. The manufacturing, processing, and applications of ceramic greentapes are described generally in Richard E. Mistler, "Tape Casting: The Basic Process for Meeting the Needs of the Electronics Industry," Ceramic Bulletin, vol. 69, no. 6, pp. 1022–26 (1990), and in U.S. Pat. No. 3,991,029, which are incorporated herein by reference.

In electronic applications, one or more of the green-tape layers may include metallized portions to provide conduction pathways for electrical current in the finished multilayered structure. For microchannel or microfluidic devices, the green-tape layers may also have portions punched out to define vias, channels, or cavities, which may define fluid pathways.

Conventional lamination processes generally require lamination at high pressure. Typically, the lamination process occurs in two steps. First, the stacked layers of green-tape are subjected to about 1000 to 1500 psi in a uniaxial press. Next, the layers are subjected to about 3000 to 5000 psi in an isostatic press for about 10 to 15 minutes at an elevated temperature, such as 70° C.

This conventional lamination process has a number of limitations. For example, the relatively long period of time required in the isostatic press is undesirable in a large scale manufacturing process.

Additionally, such high pressures tend to distort the dimensions of internal structures present in the layers and can damage certain materials and devices, which may be desired to be included in the finished multilayered structure. Control over the dimensions of internal structures is also undesirably low when such high pressures are used. The problem is particularly acute when structures such as internal or external cavities or channels are desired to be formed in the multilayered structure, as such structures tend to close up when such high pressures are applied. The problem is more acute the larger the cavity or channel is. Accordingly, the formation of all but the very smallest internal cavities and channels, i.e., those with sizes less than about 20 microns, in the multilayered structure is very difficult to do reliably when such high pressures are used for lamination.

SUMMARY OF THE INVENTION

In a first principal aspect, the present invention is a method for fabricating a multilayered structure from a plurality of green-tapes, wherein a room-temperature adhesive, i.e., an adhesive that has a glass transition temperature below room temperature, is applied to the green-tapes. The green-tapes are then stacked together to form a multilayered green-tape structure. The room-temperature adhesive binds the green-tapes by penetrating the surfaces of adjacent green-tapes. The multilayered green-tape structure is then fired to achieve a predetermined sintering temperature for a predetermined amount of time to form the multilayered structure.

In a second principal aspect, the present invention is a method for fabricating a multilayered structure from a plurality of green-tapes, wherein an adhesive having a polymer different from the polymer binder of the green-tapes is applied to the green-tapes. The green-tapes are stacked to form a multilayered structure, which is then fired to achieve a predetermined sintering temperature for a predetermined amount of time to form the multilayered structure.

In a third principal aspect, the present invention is the multilayered structure fabricated by these methods.

In another aspect, the present invention provides a method for fabricating a substantially monolithic structure from a plurality of green-tape layers including at least a first green-tape layer and a second green-tape layer. The method includes applying an adhesive to a first surface of said first green-tape layer, wherein said adhesive has a glass transition temperature below room temperature. The method further includes laminating said first or second green-tape layer with at least a third green-tape layer, including applying a pressure exceeding 2500 psi, prior to contacting said second green-tape layer to said first green-tape layer, such that said adhesive interposes said first surface of said first green-tape layer and a second surface of said second green-tape layer, thereby binding said first green-tape layer to said second green-tape layer. The method optionally includes repeating the applying and contacting steps to add additionally green-tape layers to the multilayered green-tape structure. The green-tape structure is laminated at a pressure of less than 2500 psi and fired, thereby forming said substantially monolithic structure.

It is the primary an object of the present invention to provide a method for fabricating a multilayered structure without the application of high pressures.

It is also an object of the present invention to provide a method for fabricating a multilayered structure that is practical to apply in a large scale manufacturing operation.

It is a further object of the present invention to provide a method for fabricating a multilayered structure that minimizes deformation of and damage to internal structures.

Still another object of the present invention is to provide a method for forming cavities and channels in a multilayered structure with good dimensional tolerances.

Yet another object of the present invention is to provide a multilayered structure that includes internal electrical and fluid pathways and a method for fabricating such a structure.

DETAILED DESCRIPTION OF THE INVENTION

The method begins with providing sheets of green-tape that are preferably 50 to 250 microns thick. The green-tape is a composite material that includes inorganic particles of glass, glass-ceramic, ceramic, metal, or mixtures thereof, dispersed in a polymer binder, and may also include additives such as plasticizers and dispersants. The ceramic particles are typically metal oxides, such as aluminum oxide or zirconium oxide. An example of such a green-tape that includes glass-ceramic particles is "AX951" that is sold by E. I. Du Pont de Nemours and Company. An example of a green-tape that includes aluminum oxide particles is "Ferro Alumina" that is sold by Ferro Corp. The composition of the green-tape may also be custom formulated to meet particular applications.

The sheets of green-tape are cut to the desired size, typically 6 inches by 6 inches for conventional processing. Each green-tape layer may then be textured using various techniques to form desired structures, such as vias, channels, or cavities, in the finished multilayered structure.

As used herein, the term "via" refers to a hole formed in a green-tape sheet. Typical vias have diameters ranging from 100 to 500 microns. Vias may also be filled in subsequent steps with other materials, such as metallic pastes.

As used herein, the term "channel" refers to an open region within a multilayered structure that has its length greater than its diameter. Typical channels have diameters ranging from under 100 microns to 500 microns. In microchannel and microfluidic devices, channels may be used to transfer materials, such as gases or fluids. "Channels" may also be referred to as "capillaries" or "conduits."

As used herein, the term "cavity" refers to a hole or open area, such as in a microchannel or microfluidic device, which may be used to contain, mix, react, or transfer materials, such as gases or fluids. Typically, cavities are connected to a channel or a via to provide input or output of material, and, in such cases, the cavity has dimensions greater than that of the channel or via. "Cavities" may also be referred to as "wells."

Various techniques may be used to texture a green-tape layer. For example, portions of a green-tape layer may be punched out to form vias or channels. This operation may be accomplished using conventional multilayer ceramic punches, such as the Pacific Trinetics Corp. Model APS-8718 Automated Punch System. Instead of punching out part of the material, features, such as channels and wells may be embossed into the surface of the green-tape by pressing the green-tape against an embossing plate that has a negative image of the desired structure. Texturing may also be accomplished by laser tooling with a laser via system, such as the Pacific Trinetics LVS-3012.

Conductive materials may also be applied to each green-tape layer to provide electrical transmission lines in the finished multilayered structure. Preferably, thick film pastes are used as the conductive material, because during the firing of the multilayered structure, the pastes sinter with the to form an integrated and reliable assembly. The thick film pastes typically include metal particles, such as silver, platinum, palladium, gold, copper, tungsten, nickel, tin, or alloys thereof. Silver pastes are preferred. Examples of suitable silver pastes are silver conductor composition numbers 7025 and 7713 sold by E. I. Du Pont de Nemours and Company.

The conductive materials may be applied to a green-tape layer by screen-printing. In the screen-printing process, the conductive material is forced through a patterned silk screen so as to be deposited onto the green-tape layer in a corresponding pattern. Typically, the silk screen pattern is created photographically by exposure to a mask. Additionally, vias present in the green-tape layer may be filled with the conductive material to provide electrical connections between layers.

Many other materials may be added to the green-tape layers to provide desired functionalities. For example, resistive and dielectric materials may be added to patterned green-tape layers to form resistors and capacitors, respectively, in the finished device. Optical materials, such as fused silica, quartz, or glass, may be incorporated into the green-tape layers and then co-fired to provide optical windows. Alternatively, polymeric optical materials may be formed in the multilayered structure by incorporating a monomer into channels after the structure is fired and then polymerizing it. Other materials that may be added include, without limitation, catalytic materials, piezoelectric materials, and magnetic materials.

After the desired structures are formed in each layer of green-tape, a layer of adhesive is applied to either surface of the green-tape. Preferably, the adhesive is a room-temperature adhesive. Such room-temperature adhesives have glass transition temperatures below room temperature, i.e., below about 20° C., so that they can bind substrates together at room temperature. Moreover, rather than undergoing a chemical change or chemically reacting with or dissolving components of the substrates, such room-temperature adhesives bind substrates together by penetrating into the surfaces of the substrates. Sometimes such room-temperature adhesives are referred to as "pressure-sensitive adhesives." Suitable room-temperature adhesives are typically supplied as water-based emulsions and are available from Rohm and Haas, Inc. and from Air Products, Inc. For example, a material sold by Air Products, Inc. as "Flexcryl 1653" has been found to work well.

The room-temperature adhesive may be applied to the green-tape by conventional coating techniques. To facilitate coating, it is often desirable to dilute the supplied pressure-sensitive adhesive in water, depending on the coating technique used and on the viscosity and solids loading of the starting material. After coating, the room-temperature adhesive is allowed to dry. The dried thickness of the film of room-temperature adhesive is preferably in the range of 1 to 10 microns, and the thickness should be uniform over the entire surface of the green-tape. Film thicknesses that exceed 15 microns are undesirable. With such thick films of adhesive voiding or delamination can occur during firing, due to the large quantity of organic material that must be removed. Films that are less than about 0.5 microns thick when dried are too thin because they provide insufficient adhesion between the layers.

From among conventional coating techniques, spin-coating and spraying are the preferred methods. If spin-coating is used, it is preferable to add 1 gram of deionized water for every 10 grams of "Flexcryl 1653." If spraying is used, a higher dilution level is preferred to facilitate ease of spraying. Additionally, when room-temperature adhesive is sprayed on, it is preferable to hold the green-tape at an elevated temperature, e.g., about 60 to 70° C., so that the material dries nearly instantaneously as it is deposited onto the green-tape. The instantaneous drying results in a more uniform and heterogeneous film of adhesive.

After the room-temperature adhesive has been applied to the green-tape layers, the layers are stacked together to form a multilayered green-tape structure. Preferably, the layers are stacked in an alignment die, so as to maintain the desired registration between the structures of each layer. When an alignment die is used, alignment holes must be added to each green-tape layer.

Typically, the stacking process alone is sufficient to bind the green-tape layers together when a room-temperature adhesive is used. In other words, little or no pressure is required to bind the layers together. However, in order to effect a more secure binding of the layers, the layers are preferably laminated together after they are stacked.

The lamination process involves the application of pressure to the stacked layers. Pressures less than 2500 psi are preferable in order to achieve good control over the dimensions of such structures as internal or external cavities and channels. However, lower pressures are more desirable to allow the formation of larger structures, such as cavities and channels. For example, if a lamination pressure of 2500 psi is used, the size of well-formed internal cavities and channels is typically limited to no larger than roughly 20 microns. Accordingly, pressures less than 1000 psi are more preferred, as such pressures generally enable structures having sizes greater than about 100 microns to be formed with some measure of dimensional control. Pressures of less than 300 psi are even more preferred, as such pressures typically allow structures with sizes greater than 250 microns to be formed with some degree of dimensional control. Pressures less than 100 psi, which are referred to herein as "near-zero pressures," are most preferred, because at such pressures few limits exist on the size of internal and external cavities and channels that can be formed in the multilayered structure.

The pressure is preferably applied in the lamination process by means of a uniaxial press. However, pressures less than about 100 psi can also be applied by hand.

As with semiconductor device fabrication, many devices may be present on each sheet. Accordingly, after lamination the multilayered structure may be diced using conventional green-tape dicing or sawing apparatus to separate the individual devices. The high level of peel and shear resistance provided by the room-temperature adhesive results in the occurrence of very little edge delamination during the dicing process. If some layers become separated around the edges after dicing, the layers may be easily relaminated by applying pressure to the affected edges by hand, without adversely affecting the rest of the device.

The final processing step is firing to convert the laminated multilayered green-tape structure from its "green" state to form the finished multilayered structure. Typically, the multilayered structure is a multilayered ceramic structure formed from ceramic green-tapes.

The firing process occurs in two important stages as the temperature is raised. The first important stage is the binder burnout stage that occurs in the temperature range of about 250 to 500° C. in which the binder and other organic material is removed from the structure.

In the next important stage, the sintering stage, which occurs at a higher temperature, the inorganic particles sinter together so that the multilayered structure is densified to become a homogeneous structure. The sintering temperature used depends on the nature of the inorganic particles present in the green-tape. For many types of ceramics, appropriate sintering temperatures range from about 950 to about 1600° C., depending on the material. For example, for green-tape containing aluminum oxide, sintering temperatures between 1500 and 1600° C. are typical. Other ceramic materials, such as silicon nitride, aluminum nitride, and silicon carbide, require higher sintering temperatures, namely 1700 to 2200° C. For green-tape with glass-ceramic particles, a sintering temperature in the range of 750 to 950° C. is typical. Glass particles generally require sintering temperatures in the range of only about 350 to 700° C. Finally, metal particles may require sintering temperatures anywhere from 550 to 1700° C., depending on the metal.

Typically, the devices are fired for a period of about 4 hours to about 12 hours or more, depending on the material used. Generally, the firing should be of a sufficient duration so as to remove the organic materials from the structure and to completely sinter the inorganic particles. In particular, polymers are present as a binder in the green-tape and in the room-temperature adhesive. The firing should be of sufficient temperature and duration to decompose these polymers and to allow for their removal from the multilayered structure.

Typically, the multilayered structure undergoes a reduction in volume during the firing process. During the binder burnout phase, a small volume reduction of about 0.5 to 1.5% is normally observed. At higher temperatures, during the sintering stage, a further volume reduction of about 14 to 17% is typically observed.

Figure 1:
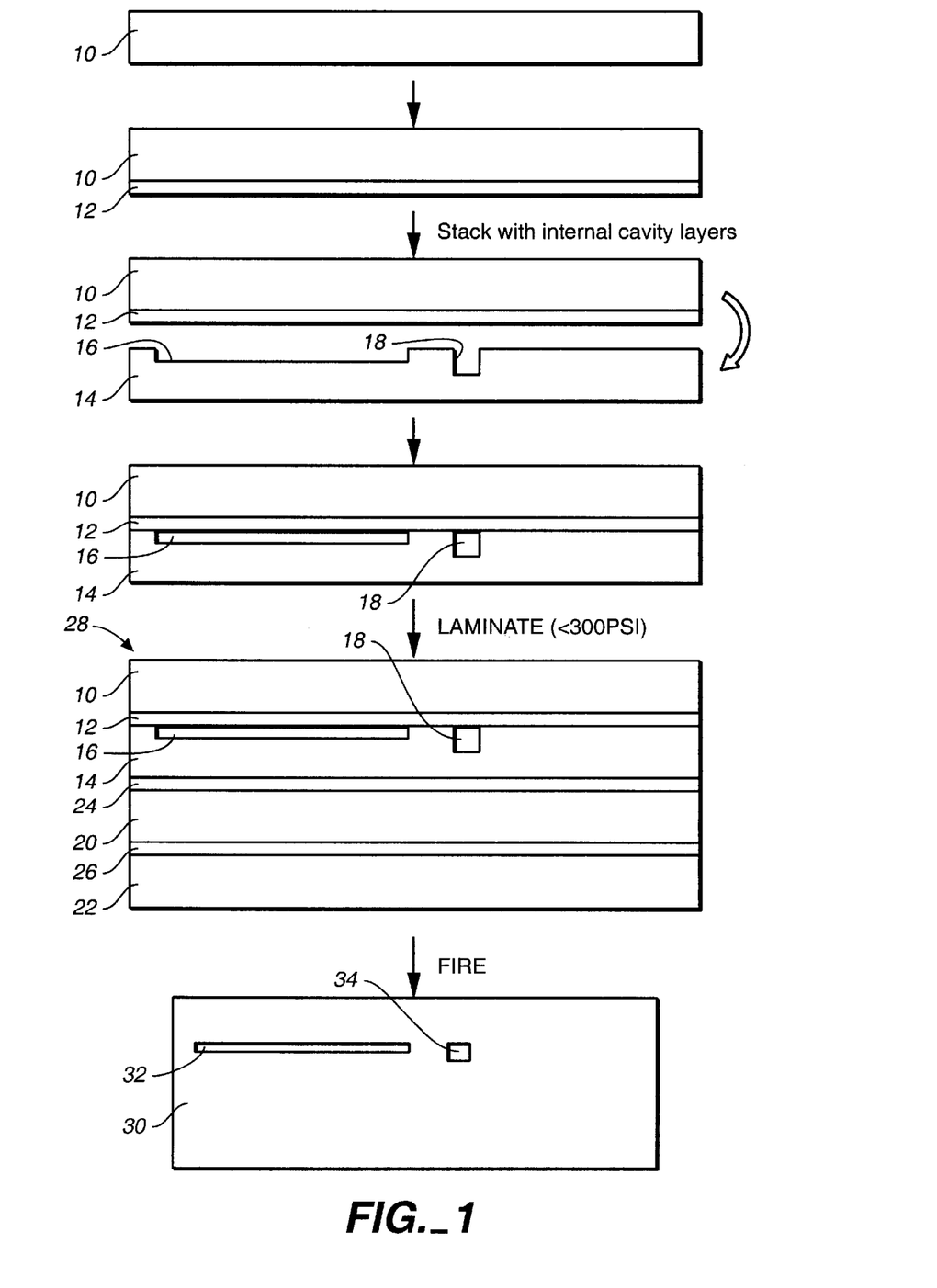
FIG. 1 is a schematic representation of a method for making a multilayered structure in accordance with the present invention.

FIG. 1 summarizes the aforementioned steps, schematically illustrating crosssections of typical layers that would be used to form a multilayered structure in accordance with the present invention. A first green-tape layer 10 is provided with a size appropriate for further processing. A room-temperature adhesive layer 12 is applied to one surface of green-tape 10. First green-tape layer 10 is then stacked with a second green-tape layer 14, which has already been patterned with an internal channel 16 and an internal cavity 18. These layers are then stacked with two more green-tape layers 20 and 22, with associated layers of room-temperature adhesive 24 and 26, to form the complete multilayered green-tape structure 28. Multilayered green-tape structure 28 is then laminated, as described above, and fired to form the final multilayered structure 30. Significantly, the use of near-zero pressures, i.e., pressures less than 100 psi, allows the integrity of internal structures to be maintained, so that internal channel 16 and internal cavity 18 formed in green-tape layer 14 remain as an internal channel 34 and an internal cavity 34, respectively, in the final multilayered green-tape structure 30. The size of the final multilayered structure 30 is shown smaller in FIG. 1 than the size of multilayered green-tape structure 28 to reflect the volume reduction that occurs during firing.

Figure 2:
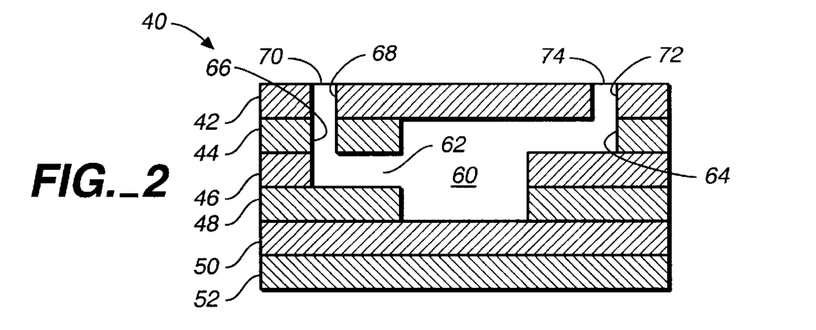
FIG. 2 is a schematic representation of a multilayered structure made in accordance with the present invention.

A cross-sectional view of a representative multilayered structure 40 which may be sed for microfluidic applications, and which is made in accordance with the present invention, is shown schematically in FIG. 2. Multilayered structure 40 is made from layers 42–52 laminated together using the near-zero pressure lamination technique of the present invention. Structure 40 includes a cavity 60 that is connected to a first channel 62 and to a second channel 64. First channel 62 is also connected to a first via 66 which, in turn, is connected to a second via 68 which defines a first fluid port 70. Second channel 64 is connected to a third via 72, which defines a second fluid port 74. In this way, cavity 60 is in fluid communication with fluid ports 70 and 74. In this configuration, ports 70 and 74 could be used as fluid input or output ports to add reactants and to remove products, with cavity 60 providing a place for reactions.

Figure 2A:
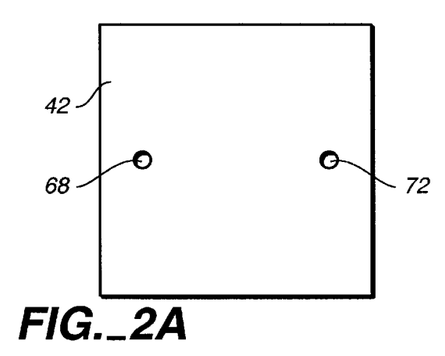
FIGS. 2A–2F are partial views of the multilayered structure of FIG. 2, with each partial view corresponding to a plan view of a distinct layer of the multilayered structure of FIG. 2.
Figure 2B:
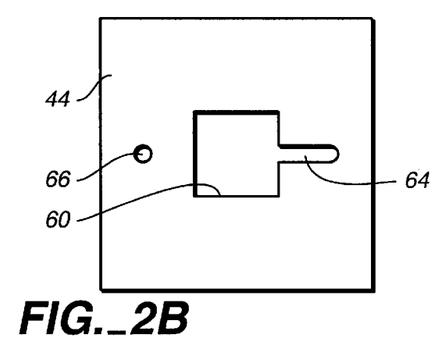
Figure 2C:
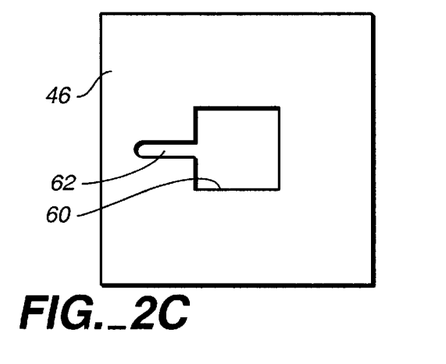
Figure 2D:
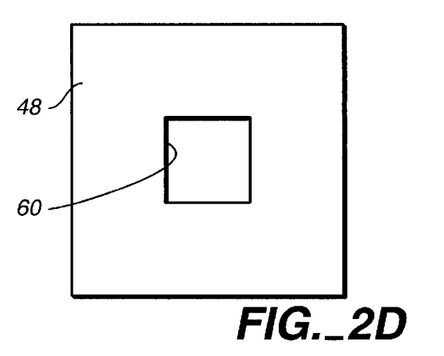
Figure 2E:
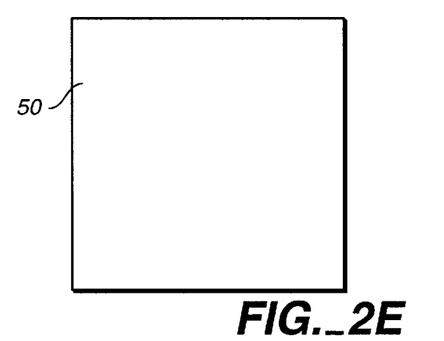
Figure 2F:
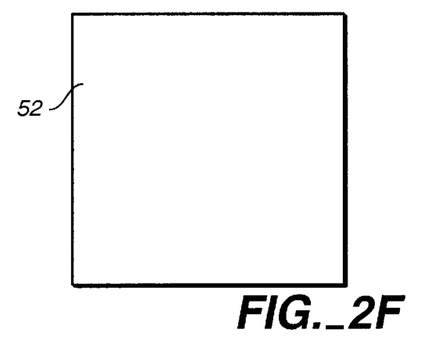

FIGS. 2A–2F are plan views of each one of layers 42–52, individually, to show what portions would be formed into each one the layers 42–52 before lamination to provide the aforementioned fluid pathways As shown in FIG. 2A, layer 42 has via 68 and via 72. As shown in FIG. 2B, layer 44 has via 66 and has a portion of cavity 60 connected to channel 64. As shown in FIG. 2C, layer 46 has a portion of cavity 60 connected to channel 62. As shown in FIG. 2D has a portion of cavity 60. Layers 50 and 52, shown in FIGS. 2E and 2F, respectively, have no such structures.

In accordance with the present invention, not every layer of the final multilayered structure needs to be laminated at near-zero pressure. For example, layers that do not contain structures or materials that would be damaged or deformed by high pressures may be laminated conventionally, and this resulting structure may then be laminated to other green-tape layers using the near-zero pressure lamination technique.

Figure 3:
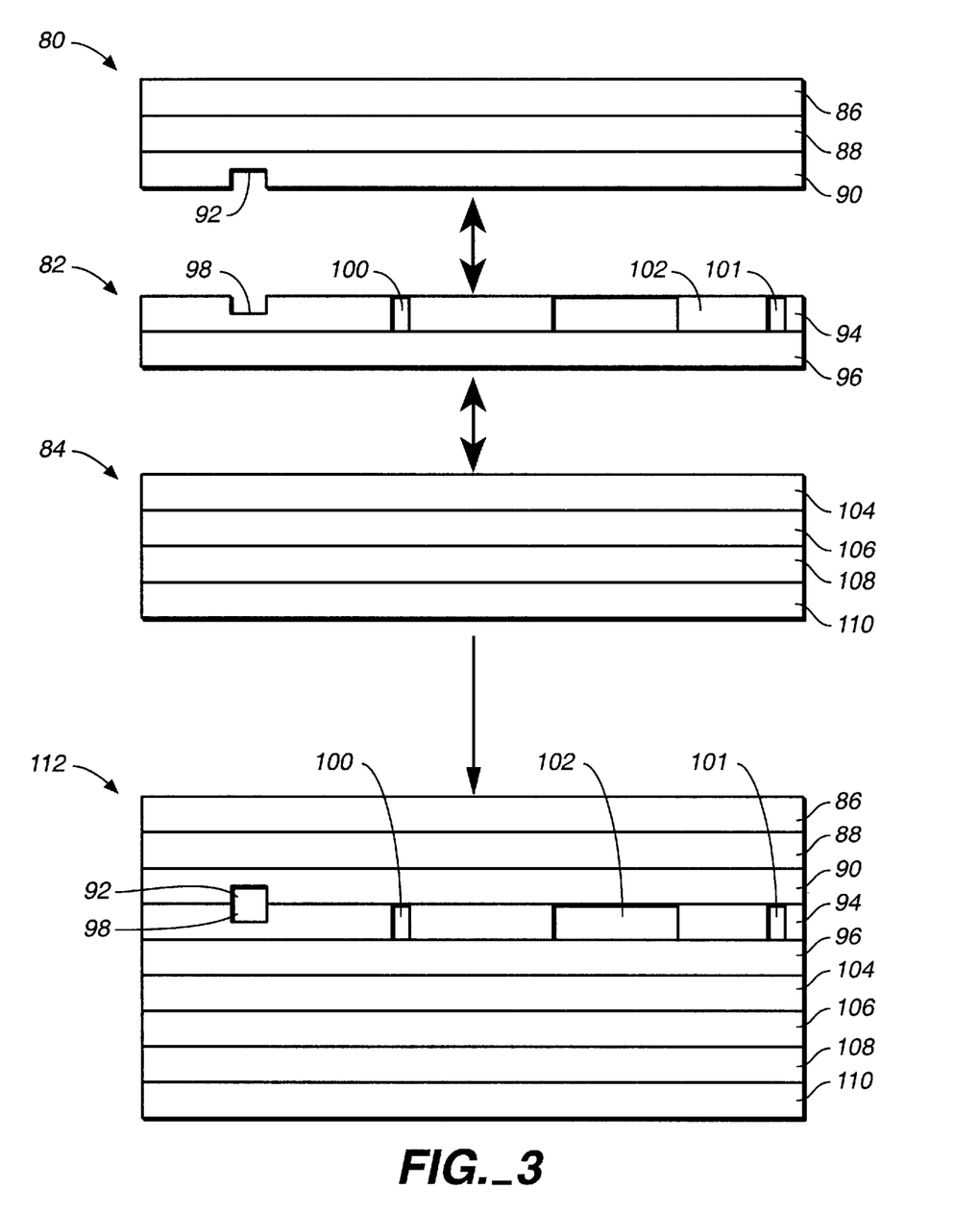
FIG. 3 is a schematic representation of an alternate method for making a multilayered structure in accordance with the present invention.

An example of such a process is shown schematically in FIG. 3. A structure 80, formed using a conventional lamination process, a structure 82, formed using the near-zero pressure lamination process, and a structure 84, formed using a conventional lamination process, are all to be laminated together. Structure 80 comprises layers 86, 88, and 90, wherein layer 90 includes a via 92. Structure 80 may be formed from any conventional lamination process that allows external vias to be preserved. Structure 82 comprises layers 94 and 96 and was formed using the near-zero pressure lamination method of the present invention. Layer 94, in turn, includes vias 98, 100, and 101, and a channel 102. Structure 84 comprises layers 104–110 and was formed using a conventional high-pressure lamination process. To form multilayered structure 112, structures 80, 82, and 84, are then laminated together using the near-zero pressure lamination process of the present invention, i.e., by applying a layer (not shown) of room-temperature adhesive to bind structures 80 and 82 and another layer (not shown) of room-temperature adhesive to bind structure 82 to structure 84.

In another aspect, the present invention provides a method for fabricating a substantially monolithic structure from a plurality of green-tape layers including at least a first green-tape layer and a second green-tape layer. The method includes applying an adhesive to a first surface of said first green-tape layer, wherein said adhesive has a glass transition temperature below room temperature. The method further includes laminating said first or second green-tape layer with at least a third green-tape layer, including applying a pressure exceeding 2500 psi, prior to contacting said second green-tape layer to said first green-tape layer, such that said adhesive interposes said first surface of said first green-tape layer and a second surface of said second green-tape layer, thereby binding said first green-tape layer to said second green-tape layer. The method optionally includes repeating the applying and contacting steps to add additionally green-tape layers to the multilayered green-tape structure. The green-tape structure is laminated at a pressure of less than 2500 psi and fired, thereby forming said substantially monolithic structure.

Figure 4:
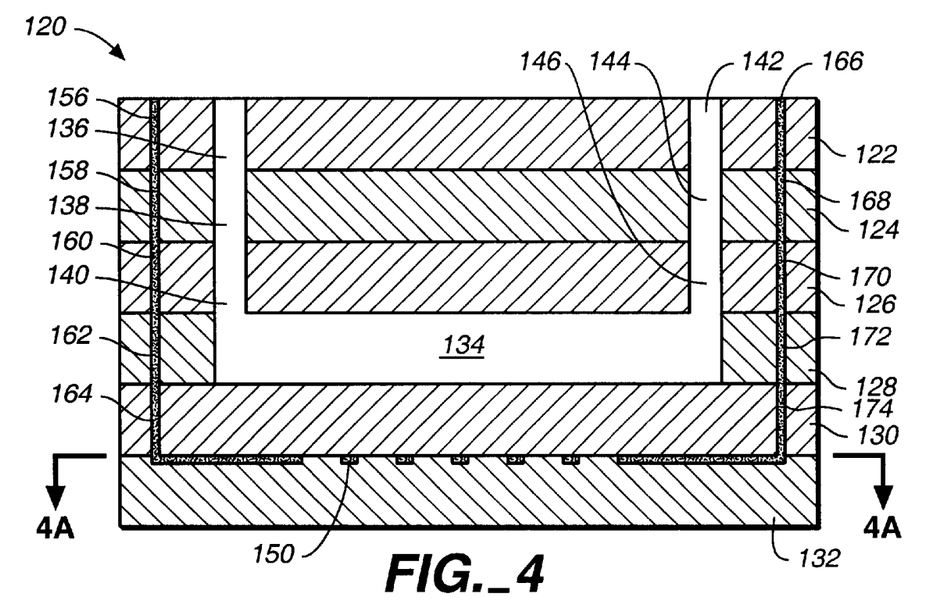
FIG. 4 is a schematic representation of a multilayered structure made in accordance with the present invention.
Figure 4A:
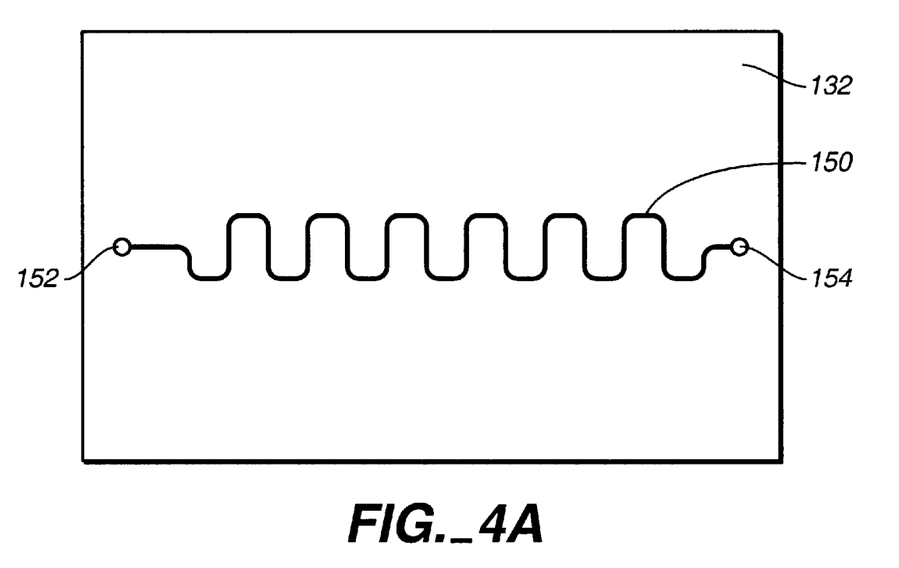
FIG. 4A is a partial view of the multilayered structure of FIG. 4, corresponding to a plan view of the bottom layer of the multilayered structure of FIG. 4.

FIG. 4 shows a representative multilayered structure 120, made in accordance with the present invention, which has both fluid and electrical pathways. Multilayered structure 120 has layers 122–132. A cavity 134 is formed in layer 132. Cavity 134 is in fluid communication with the outside by means of vias 136, 138, and 140, which are formed in layers 122, 124, and 126, respectively. Cavity 134 is also in fluid communication with the outside by means of vias 142, 144, and 146, formed in layers 122, 124, and 126, respectively. As shown in cross-sectional view in FIG. 4, and in plan view in FIG. 4A, a heater 150 is formed by a coiled trace of conductive material deposited on the surface of layer 132 and has terminals 152 and 154. Vias 156–164 are formed into layers 122–130, respectively, and are filled with a conductive material to provide an electrical conduction pathway between terminal 152 and the outside. Similarly, vias 166–174 are formed into layers 122–130, respectively, and are filled with a conductive material to provide an electrical conduction pathway between terminal 154 and the outside. In this configuration, an electrical current may be applied to heater 150 so that it maybe used to heat fluid in cavity 134.

It has been found that proper selection of the polymer in the adhesive facilitates the desired near-zero pressure lamination process. In particular, if the polymer used in the adhesive decomposes at a higher temperature than the polymer binder present in the green-tape, then the adhesive layer will promote stability of the tape interface during the firing process and will promote shorter interfacial distances between the inorganic particles of the green-tape after completion of binder burnout. The reduced inter-particle distances facilitate void-free sintering within the tape interfacial regions of the multilayered structure.

Preferably, the polymer in the adhesive should have a thermal decomposition onset and major decomposition profile about 25 to 100° C. higher than that of the polymer binder in the green-tape. This may be achieved by using an adhesive polymer that is different than the polymer binder. More particularly, it has been found that one way to achieve the desired difference in thermal decomposition profile is to choose an adhesive polymer that undergoes thermal decomposition by random scission, rather than by unzipping. The unzipping process, which is also referred to as "chain depolymerization" or "depropagation," is the successive release of monomer units from a chain end or weak link. The random scission process, which is also referred to as "random degradation," occurs by chain rupture at random points along the chain.

Polymers that undergo random scission generally have a thermal decomposition profile that is extended relative to that of polymers that decompose by unzipping. Often, the temperature of half decomposition, i.e., the temperature at which the weight loss during pyrolysis at a constant rate of temperature rise reaches 50% of its final value, and the temperature of maximum rate of decomposition are both about 25 to 100° C. higher for polymers that undergo random scission, as compared to polymers that undergo unzipping. Moreover, the polymer binder of many kinds of green-tape is predominantly an acrylic polymer, an acrylic copolymer, or a blend of acrylic polymers and copolymers, all of which decompose by unzipping. Accordingly, choosing an adhesive with a random scission polymer will tend to greatly strengthen the interfacial bond during the firing process. Such random scission polymers include polymers and copolymers that have an ethylene main-chain group, such as vinyl acetate-ethylene or ethylene-vinyl acrylic copolymer.

Figure 5:
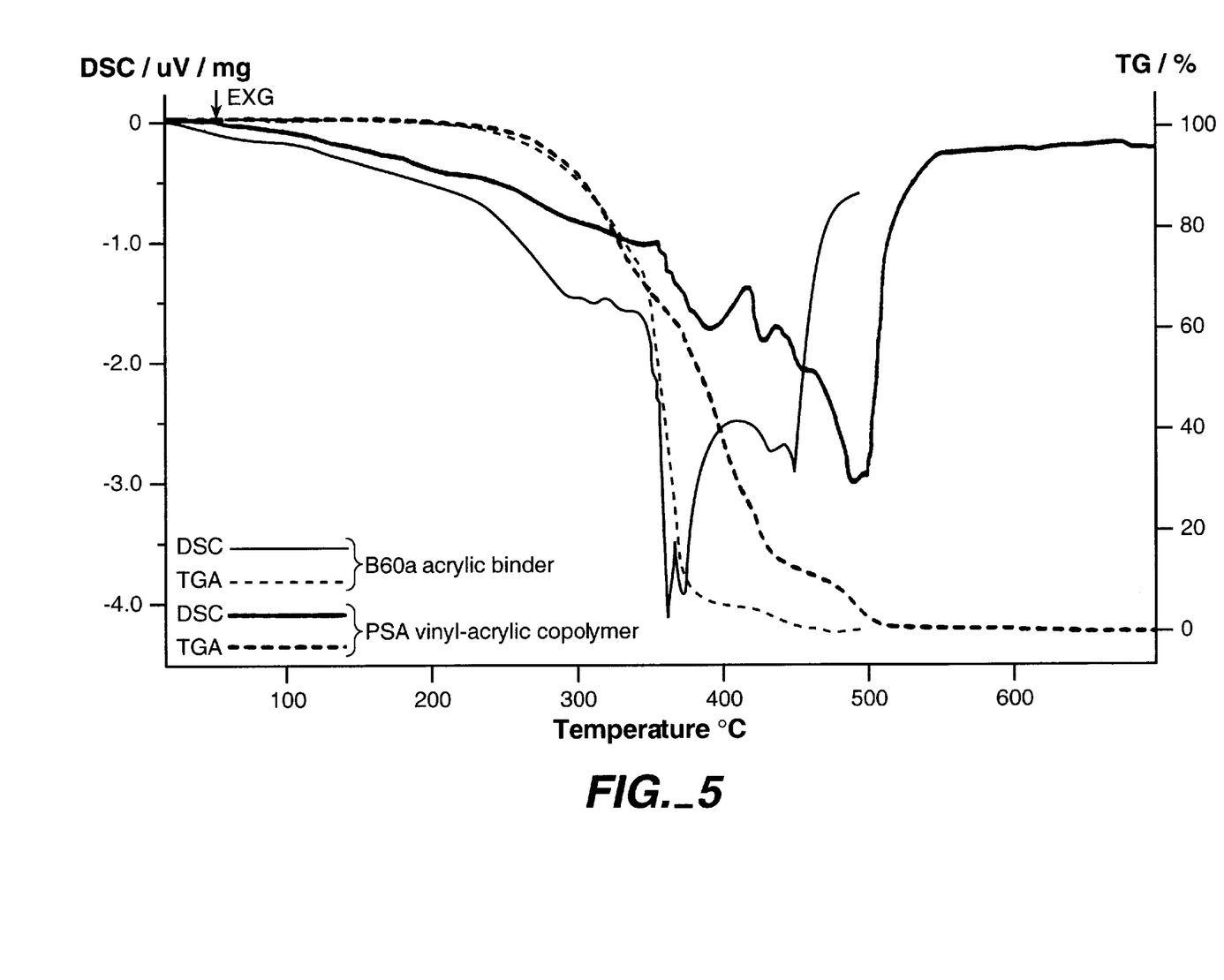
FIG. 5 is a graphical comparison of the thermal decomposition of an acrylic binder used in the green-tapes of the present invention and an adhesive polymer used in the present invention.

FIG. 5 compares the thermal decomposition of an ethylene-vinyl acrylic copolymer (designated "PSA vinyl-acrylic copolymer"), which undergoes random scission, with an acrylic binder used in green-tapes ("designated B60a acrylic binder"), which undergoes unzipping, as measured thermogravimetrically (the curves designated "TGA") and by differential scanning calorimetry (the curves designated "DSC"). As is apparent from FIG. 5, in the temperature range from about 350 to 400° C. the acrylic binder undergoes rapid decomposition and removal, whereas the room-temperature adhesive polymer decomposes much more gradually. In fact, in this example at 375° C. less than 10% of the acrylic binder remains, whereas more than 60% of the adhesive polymer remains. Accordingly, in this temperature range the room-temperature adhesive will maintain a strong bond between the layers while the binder within the green-tape layers is burned off.

Although various embodiments of this invention have been shown and described, it should be understood that various modifications and substitutions, as well as rearrangements and combinations of the preceding embodiments, can be made by those skilled in the art, without departing from the novel spirit and scope of this invention.

What is claimed is:

1. A method for fabricating a substantially monolithic structure from a plurality of green-tape layers including at least a first green-tape layer and a second green-tape layer, the method comprising:
   (a) applying an adhesive to a first surface of said first green-tape layer, wherein said adhesive has a glass transition temperature below room temperature;
   (b) laminating said first green-tape layer with at least a third green-tape layer, including applying a pressure exceeding 2500 psi, prior to contacting said second green-tape layer to said first green-tape layer, such that said adhesive interposes said first surface of said first green-tape layer and a second surface of said second green-tape layer, thereby binding said first green-tape layer to said second green-tape layer;
   (c) optionally repeating steps (a) and (b) to add additional green-tape layers to said multilayered green-tape structure;
   (d) laminating said green-tape structure at a pressure of less than 2500 psi; and
   (e) firing said multilayered green-tape structure, thereby forming said substantially monolithic structure.

2. The method of claim 1, further comprising texturing at least one of said plurality of green-tape layers.

3. The method of claim 2, wherein said texturing includes punching out a portion of said at at least one of said plurality of green-tape layers.

4. The method of claim 2, wherein said texturing includes embossing a portion of said at least one of said plurality of green-tape layers.

5. The method of claim 2, wherein said texturing includes laser tooling a portion of said at least one of said plurality of green-tape layers.

6. The method of claim 1, further comprising adding a conductive material to at least one of said plurality of green-tape layers.

7. The method of claim 6, wherein said conductive material includes a metal containing paste.

8. The method of claim 1, wherein at least one of said green-tape layers include glass particles.

9. The method of claim 1, wherein at least one of said green-tape layers include glass ceramic particles.

10. The method of claim 1, wherein at least one of said green-tape layers include ceramic particles.

11. The method of claim 10, wherein said ceramic particles include metal oxide particles.

12. The method of claim 11, wherein said metal oxide particles are selected from the group consisting of aluminum oxide particles and zirconium oxide particles.

13. The method of claim 1, wherein at least one of said green-tape layers include metal particles.

14. The method of claim 1, wherein said plurality of green-tape layers include a polymer binder and said adhesive includes an adhesive polymer.

15. The method of claim 14, wherein said adhesive polymer has a temperature of half decomposition that is higher than the temperature of half decomposition of said polymer binder.

16. The method of claim 15, wherein said adhesive polymer has a temperature of half decomposition that is 25 to 100° C. higher than the temperature of half decomposition of said polymer binder.

17. The method of claim 14, wherein said adhesive polymer has a temperature of maximum rate of decomposition that is higher than the temperature of maximum rate of decomposition of said polymer binder.

18. The method of claim 17, wherein said adhesive polymer has a temperature of maximum rate of decomposition that is that is 25 to 100° C. higher than the temperature of maximum rate of decomposition of said polymer binder.

19. The method of claim 14, wherein said polymer binder undergoes thermal decomposition predominantly by unzipping and said adhesive polymer undergoes thermal decomposition predominantly by random scission.

20. The method of claim 19, wherein said adhesive polymer includes a polymer that has an ethylene main-chain group.

21. The method of claim 20, wherein said adhesive polymer includes a polymer selected from the group consisting of vinyl acetate-ethylene and ethylene-vinyl acrylic copolymer.

22. The method of claim 19, wherein said polymer binder includes a polymer selected from the group consisting of acrylic polymers and acrylic copolymers.

23. The method of claim 1, wherein said pressure for laminating said green-tape structure is uniaxial pressure and is less than 1000 psi.

24. The method of claim 23, wherein said pressure for laminating said green-tape structure is uniaxial pressure and is less than 300 psi.

25. The method of claim 24, wherein said pressure for laminating said green-tape structure is uniaxial pressure and is less than 100 psi.

26. The method of claim 1, further comprising laminating said second green-tape layer with at least a third green-tape layer prior to step (b).

27. The method of claim 1, wherein said firing includes heating said multilayered green-tape structure to temperatures in the range of about 250 to 500° C. to remove organic components from said laminated multilayered green-tape structure.

28. A method for fabricating a substantially monolithic structure from a plurality of green-tape layers including at least a first green-tape layer and a second green-tape layer, the method comprising:

(a) applying an adhesive to a first surface of said first green-tape layer, wherein said adhesive has a glass transition temperature below room temperature;

(b) laminating said second green-tape layer with at least a third green-tape layer, including applying a pressure exceeding 2500 psi, prior to contacting said second green-tape layer to said first green-tape layer, such that said adhesive interposes said first surface of said first green-tape layer and a second surface of said second green-tape layer, thereby binding said first green-tape layer to said second green-tape layer;

(c) optionally repeating steps (a) and (b) to add additional green-tape layers to said multilayered green-tape structure;

(d) laminating said green-tape structure at a pressure of less than 2500 psi; and (e) firing said multilayered green-tape structure, thereby forming said substantially monolithic structure.

* * * * *